United States Patent
O'Leary et al.

(10) Patent No.: US 7,712,350 B2
(45) Date of Patent: May 11, 2010

(54) APPARATUS AND METHOD FOR DETERMINING DENSITY OF INSULATION

(75) Inventors: Robert J. O'Leary, Newark, OH (US); Steven G. Schmitt, Newark, OH (US); Jacob T. Chacko, Pickerington, OH (US)

(73) Assignee: Owens Corning Intellectual Captial, LLCDE (US)

( * ) Notice: Subject to any disclaimer, the term of this patent is extended or adjusted under 35 U.S.C. 154(b) by 79 days.

(21) Appl. No.: 11/818,129

(22) Filed: Jun. 13, 2007

(65) Prior Publication Data

US 2008/0236276 A1 Oct. 2, 2008

Related U.S. Application Data

(62) Division of application No. 10/969,427, filed on Oct. 20, 2004, now abandoned.

(51) Int. Cl.
*G01N 9/00* (2006.01)
*G01N 15/08* (2006.01)

(52) U.S. Cl. .............................. 73/32 R; 73/38; 73/438
(58) Field of Classification Search ................. 73/32 R, 73/38, 438
See application file for complete search history.

(56) References Cited

U.S. PATENT DOCUMENTS

| | | | |
|---|---|---|---|
| 2,755,660 A | 7/1956 | Kammermeyer et al. |
| 2,912,851 A | 11/1959 | Karnes |
| 3,524,342 A | 8/1970 | Hobbs |
| 3,590,634 A | 7/1971 | Pasternak et al. |
| 3,788,125 A | 1/1974 | Kirchstein et al. |
| 3,808,876 A | 5/1974 | Kershaw |
| 4,052,885 A | 10/1977 | Shuck |
| 4,095,454 A | 6/1978 | Fisher |
| 4,177,618 A | 12/1979 | Felter |
| 4,207,674 A | 6/1980 | Heronema |

(Continued)

FOREIGN PATENT DOCUMENTS

GB 2 103 695 2/1983

OTHER PUBLICATIONS

"The Evolution of Insulation Continues as Owens Corning Previews Three New Products at the 2004 International Builder Show", Jan. 19, 2004, available on the internet at <http://owenscorning.mediaroom.com/index.php?s=press_releases&item=99>.*

(Continued)

*Primary Examiner*—David A. Rogers
(74) *Attorney, Agent, or Firm*—James J. Dottavio; Jason S. Fokens

(57) ABSTRACT

An apparatus for determining the density of insulation in a cavity of a structure that senses a force of the insulation against the sensor. The force is used to determine the density of the insulation, which, in turn, is used to determine the thermal resistance or R-value of the insulation. The apparatus may include a fixture for supporting the sensor and holding the sensor in the substantially fixed position. A method for determining the density of loose-fill, blown-in-place insulation in a wall cavity by the use of a sensor is that measures a force exerted on the sensor by the insulation. The measured force is used to determine the density of the insulation. The thermal resistance of the insulation is determined from the known cavity depth and insulation density.

7 Claims, 8 Drawing Sheets

U.S. PATENT DOCUMENTS

| | | |
|---|---|---|
| 4,231,129 A | 11/1980 | Winch |
| 4,311,037 A | 1/1982 | Gotchel et al. |
| 4,337,666 A | 7/1982 | Bhattacharyya et al. |
| 4,401,147 A | 8/1983 | Beck et al. |
| 4,459,843 A | 7/1984 | Durham |
| 4,506,542 A | 3/1985 | Rose |
| 4,515,007 A | 5/1985 | Herman |
| 4,603,618 A | 8/1986 | Soltis |
| 4,649,738 A | 3/1987 | Waldie et al. |
| 4,676,091 A | 6/1987 | Schuster et al. |
| 4,679,423 A | 7/1987 | Ballentine |
| 4,712,347 A | 12/1987 | Sperber |
| 4,815,316 A | 3/1989 | Tantram |
| 4,854,011 A | 8/1989 | Staheli et al. |
| 4,869,197 A | 9/1989 | Gupta et al. |
| 4,911,021 A | 3/1990 | Shortridge |
| 4,979,390 A | 12/1990 | Schupack et al. |
| 5,005,403 A | 4/1991 | Steudle et al. |
| 5,036,601 A | 8/1991 | Mulle, Jr. et al. |
| 5,051,452 A | 9/1991 | Romesberg |
| 5,060,398 A | 10/1991 | Wolens |
| 5,157,960 A | 10/1992 | Brehm et al. |
| 5,192,348 A | 3/1993 | Ludwig |
| 5,209,402 A | 5/1993 | DeBra et al. |
| 5,287,674 A | 2/1994 | Sperber |
| 5,353,630 A | 10/1994 | Soda et al. |
| 5,355,653 A | 10/1994 | Henri |
| 5,373,727 A | 12/1994 | Heller et al. |
| 5,417,101 A | 5/1995 | Weich |
| 5,445,704 A | 8/1995 | Dizon |
| 5,445,792 A | 8/1995 | Rickloff et al. |
| 5,456,104 A | 10/1995 | Rosen |
| 5,485,754 A | 1/1996 | Harpster |
| 5,505,091 A | 4/1996 | Ali |
| 5,509,295 A | 4/1996 | Bartoli |
| 5,513,515 A | 5/1996 | Mayer |
| 5,594,161 A | 1/1997 | Randhahn et al. |
| 5,595,602 A | 1/1997 | Harlan |
| 5,633,453 A | 5/1997 | Johnson |
| 5,641,368 A | 6/1997 | Romes et al. |
| 5,698,772 A | 12/1997 | Deruyter et al. |
| 5,913,546 A | 6/1999 | Kuchenbrod et al. |
| 6,047,518 A | 4/2000 | Lytle |
| 6,119,506 A | 9/2000 | Gibson et al. |
| 6,330,779 B1 | 12/2001 | Kinzler |
| 6,450,009 B1 | 9/2002 | Hartikainen et al. |
| 6,463,791 B1 | 10/2002 | Berube et al. |
| 6,521,086 B2 | 2/2003 | Smith, Jr. |
| 6,568,282 B1 | 5/2003 | Ganzi |
| 6,581,451 B2 | 6/2003 | Ence et al. |
| 6,591,661 B2 | 7/2003 | Davey |
| 6,817,941 B1 | 11/2004 | Gatov |
| 6,820,819 B2 | 11/2004 | Sperber |
| 6,826,920 B2 | 12/2004 | Wacker |
| 6,928,859 B2 | 8/2005 | O'Leary |
| 7,055,370 B2 | 6/2006 | Tinianov et al. |
| 7,055,371 B2 * | 6/2006 | Babineau et al. ............ 73/32 R |
| 7,059,173 B2 | 6/2006 | Babineau, Jr. et al. |
| 7,404,260 B2 | 7/2008 | Felinger et al. |
| 2003/0217588 A1 | 11/2003 | Jalbert et al. |
| 2005/0268697 A1 | 12/2005 | Babineau et al. |
| 2007/0006664 A1 | 1/2007 | Suda et al. |
| 2007/0113650 A1 | 5/2007 | Fellinger et al. |

OTHER PUBLICATIONS

Standard Handbook for Mechanical Engineeers, Seventh Edition, pp. 14-74-14-75.

ASTM Int'l—Standard Test Methods for Thickness and Density of Blanket or Batt Thermal Insulations.

* cited by examiner

APPARATUS AND METHOD FOR DETERMINING DENSITY OF INSULATION

CROSS REFERENCE TO RELATED APPLICATIONS

This application is a divisional application of U.S. patent application Ser. No. 10/969,427 filed Oct. 20, 2004 now abandoned.

TECHNICAL FIELD AND INDUSTRIAL APPLICABILITY OF THE INVENTION

This invention relates in general to an apparatus and method for determining the density of insulation, and in particular, to an apparatus and method for determining the density of a loose-fill, blown-in-place fibrous insulation.

BACKGROUND OF THE INVENTION

In recent years, a greater emphasis has been placed on the use of insulation materials in dwellings or other structures to promote energy conservation and noise reduction At the same time, innovative architectural designs have created a variety of shapes and sizes that do not always lend themselves to the use of a conventional fibrous batting, which is often available in rolls of uniform width. This has created a need for a technique for applying fibrous insulation that does not use uniform width batting.

This need has been fulfilled to a limited extent by developing various blown-in-place insulation techniques, wherein loose-fill fibrous insulation is blown into a cavity between the flaming member's of the wall, ceiling, or floor of a dwelling. The loose-fill insulation is provides a low cost installation techniques and is perceived as capable of completely filling the cavity, regardless of its shape and size, achieving a uniform volume of insulation for optimum energy conservation, as well as sound insulation purposes.

While blown-in-place insulation techniques provide a low cost method of installing insulation, one of the advantages of batting lost to blown-in-place insulation is the batting's ability to provide a predetermined insulation value, also known as the "R-value". The R-value can be determined by the thickness (T) of the fibrous insulation and the insulation constant (k) using equation 1.

$$R = \frac{k}{T} \qquad (1)$$

In the manufacture of fiberglass batts it is a relatively simple matter to determine the nominal thickness and insulation constant to determine the R-value of the batt. This R-value is then printed on the batt during manufacture. When insulation batting is purchased, for example, to place in a new dwelling, it is often purchased by specifying a desired R-value. If installed in accordance with minimal prescribed installing techniques, the purchaser, due to uniform dimensions of insulation batting, can be count on at the insulation value having a certain thermal resistance.

The R-value of blown-in-place insulation is determined by Eq. 1 (above), however k is dependent on the density of the insulation. Therefore, one advantage of the easily determined R-value associated with batting is typically not applicable. As a consequence, it is necessary to also employ a secondary technique fox determining the density of the blown-in-place insulation for assuring that the insulation has the desired R-value.

Various secondary techniques have been employed for the determining density in blown-in-place fibrous insulations. In one technique, a known mass of loose-fill is blown into a cavity of a known volume. The mass is divided by the cavity volume to determine density and R-value. A problem with this technique is that it slows down the installation process of the insulation and therefore, may not be easily used in the field. It is also difficult to calculate the actual volume of the cavity because there are typically features such as windows, doors, devices in the area that take up volume. Further, inexperienced insulation installers may not provide an even volume filling density that causes the density and R-value to vary between cavities.

In another known technique, a space is first filled with blown-in-place insulation. Then, a sample of insulation of a known volume is removed from a wall cavity and weighed. Using the volume of the sample, it is possible to determine the density of the insulation in the cavity by weighing the sample and dividing the weight by the known volume. The R-value of the insulation may then be determined in a known manner simply by knowing the thickness of the insulation in the cavity. In some instances, the quantity of insulation may be loose or compressed. As a consequence, error in determining the density of the insulation can be magnified if care is not taken to correctly remove the sample or average a number of samples. This is also a very time consuming technique and consequently is not preferred by insulation installers.

In yet another known technique, netting is secured to wall studs to enclose an underlying cavity Insulation is blown into the cavity through a hole in the netting. The netting retains the insulation in the cavity. U.S. Pat. No. 4,712,347 to Henry V. Sperber discloses observing the bulging out of the netting as a signal that a sufficient amount of insulation has been fed into the cavity behind the netting. This technique is unreliable because it is based on the subjective observation of the insulation installer s and the tension of the netting applied to the cavities. Moreover, the mechanical properties such as the modulus of elasticity of the netting material affect the resiliency of the netting and the appearance of the bulge. In addition, the modulus of elasticity of the insulation, which is affected by the fiber diameter and the presence or absence of a binder, controls the resiliency of the insulation Environmental conditions, such as humidity, may also affect the accuracy of the technique Another disadvantage of this technique is that installers, in an effort to insure that a cavity is adequately filled, often overfill the cavity. Overfilling the cavity is undesirable because it causes the netting to bulge too much and wastes insulation. If the netting bulges too much, wallboard is difficult to install on the framing members This has been recognized as a problem and thus has led to the use of a shield during installation, whereby the shield is held against the netting while the cavity is being filled to prevent the netting from bulging undesirably.

In view of the above techniques, it is apparent that there exists a need in the art for an improved apparatus and method for installing insulation that is blown into open wall cavities to a prescribed density wherein the improved apparatus and method provide increased accuracy.

SUMMARY OF THE INVENTION

The above objects, as well as other objects not specifically enumerated, are achieved by an apparatus for determining the density of insulation in a cavity of a dwelling of other structure The apparatus is in the form of a sensor that is held within the cavity of the structure and relative to the insulation in the cavity for sensing the force of the insulation against the sensor. The force is used to determine the density of the insulation, which, in turn, is used to determine the thermal resistance or R-value of the insulation.

An alternative apparatus includes a sensor and a fixture supporting the sensor The fixture is structured and dimensioned to hold the sensor against the insulation within the cavity to measure a material property of the insulation and therefore determine density and R-value The material property may be resistance to an applied force, pressure within the cavity, resistance to air flow, or any other material property that may be used effectively to calculate density or R-value.

A method for determining the density of loose-fill, blown-in-place insulation comprises the initial step of providing a structure that includes flaming members and a sheath forming at least one cavity having a known depth. An exposed side of the cavity is covered with netting. The cavity is then filled with insulation. A sensor is held in contact with the netting or the insulation in the cavity The sensor then detects a material property of the insulation that may be converted to a density or R-value. For example, a force may be exerted by the sensor on the insulation. The force may include mechanical force, air pressure differential, ultra-sonic response or any other force that may be used to calculate density. The thermal resistance of the insulation is determined from the known cavity depth and insulation density.

Various objects and advantages of this invention will become apparent to those skilled in the art from the following detailed description of the preferred embodiment, when read in light of the accompanying drawings.

DETAILED DESCRIPTION AND PREFERRED EMBODIMENTS OF THE INVENTION

Figure 1:
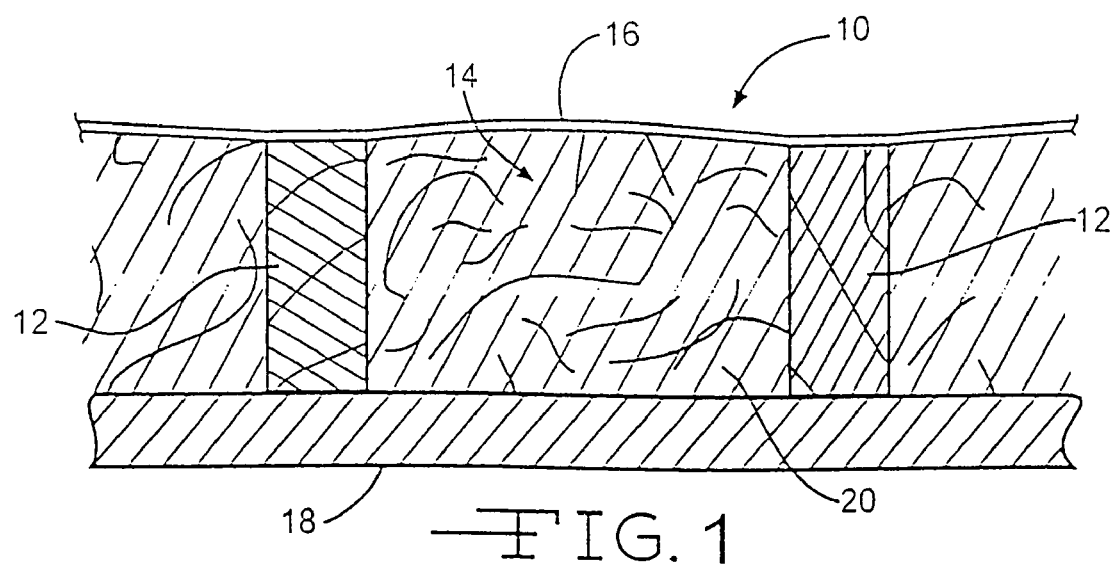
FIG. 1 is a diagrammatic representation in plan of a partial structure of a dwelling or other structure.

Referring now to the drawings, there is illustrated in FIG. 1 a partial structure of a dwelling or other structure, indicated generally at 10, including flaming members 12, such as wall studs, ceiling joists, or floor joists. Various other flaming members, not shown, the purpose of which will be apparent to those skilled in the art, maybe included in the structure 10. A cavity 14 is formed between the framing members 12. An inner side of the cavity 14 is covered with a sheet or netting 16. An outer side of the cavity 14 is covered with an exterior sheathing 18, which sheathes the structure 10 except at locations of doors and windows, not shown.

Insulation 20 is installed in the cavity 14 to prevent heat passage either outwardly or inwardly through the structure, and to minimize sound transmission therethrough The insulation 20 is preferably a loose-fill, blown-in-place fibrous insulation. The insulation 20 may consist of any suitable material useful for insulation purposes. Such insulation 20 may be installed in a conventional manner, such as through use of a blower apparatus, not shown, which picks up the insulation in an air stream and carries the insulation to the cavity 14 through a tube or hose, also not shown.

The netting 16 is preferably relatively thin, yet are capable of containing the insulation 20 in the cavity 14 to hold the insulation 20 in place, and serves to permit air to escape from the cavity 14 while filling the cavity 14 with insulation 20. The netting 16 terminates at lower and upper ends of the cavity 14 at flaming members, such as a sill plate and a header, not shown, that traverse the flaming members 12.

Figure 2:
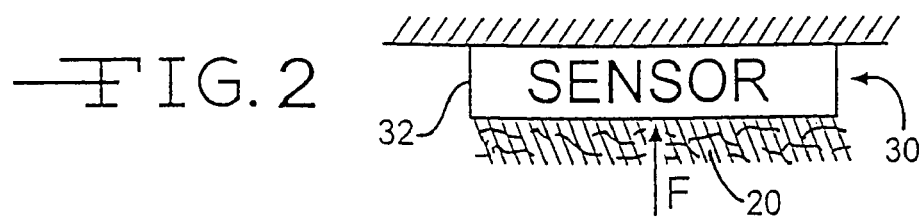
FIG. 2 is a schematic representation in plan of an apparatus for determining the density of a loose-fill, blown-in-place fibrous insulation in a cavity of the structure illustrated in FIG. 1.

An apparatus for determining the density of insulation 20 in the cavity 14 is schematically represented at 30 in FIG. 2. The determination of density leads to the determination of thermal resistance, or the R-value, of the insulation 20. The apparatus 30 comprises a sensor 32 that is adapted to be held in a substantially fixed position relative to the insulation 20 in the cavity 14 The term "substantially" with respect to the term "fixed" means that the sensor 32 will be held in a position relative to the insulation that allows reliable density determinations to be repeatedly made by the sensor 32. That is to say, the sensor 32 may suffer some minor deviation in position as long as the density determinations remain reliable.

According to the present invention, the sensor 32 senses force F, or a change in force, which is used to determine density, as will be described in greater detail in the description hereinbelow. Numerous embodiments of the apparatus 30 can be used to catty out the invention Some examples of such embodiments are set forth in the following paragraphs.

Figure 3A:
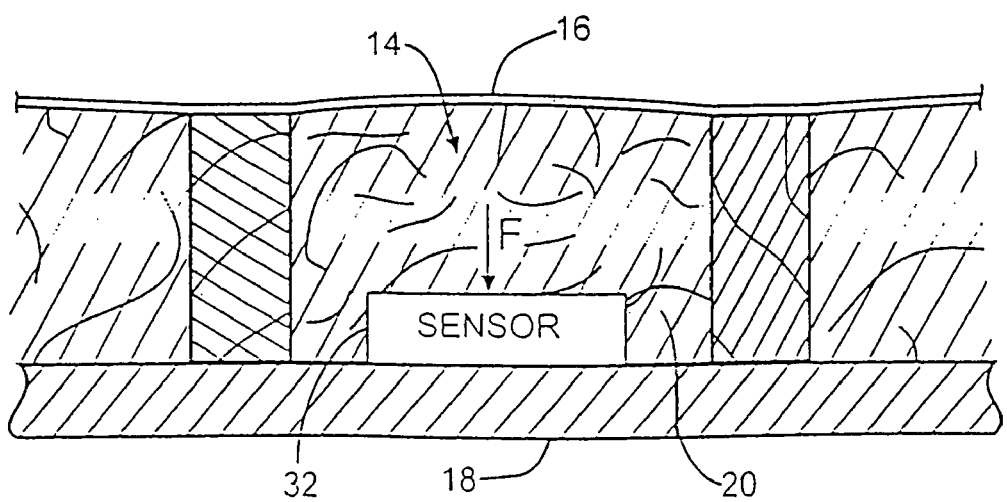
FIGS. 3A and 3B are diagrammatic representations in plan of sensors of the apparatus according to the invention supported within the cavity of the structure illustrated in FIG. 1.
Figure 3B:
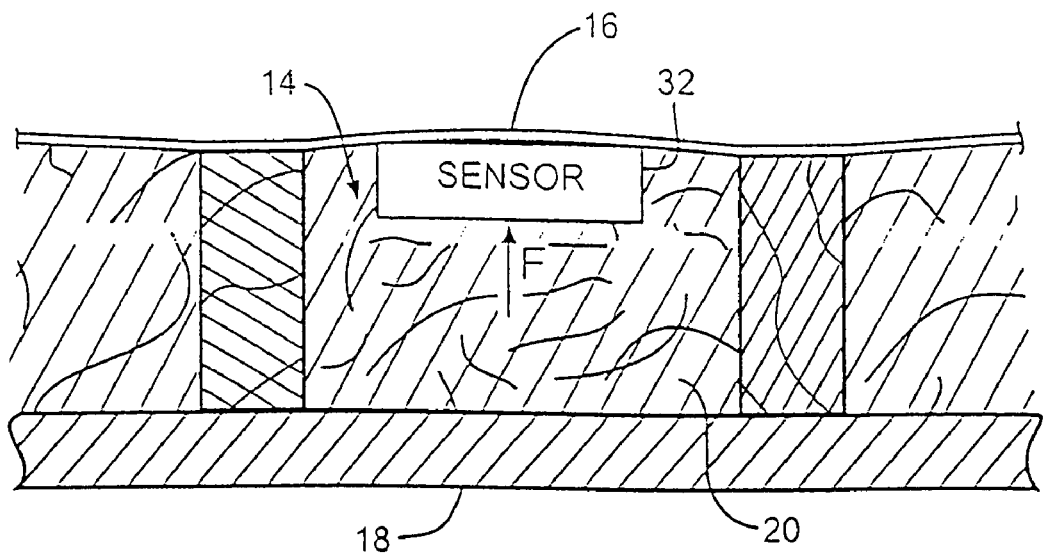

In one embodiment of the invention, the sensor 32 is supported within the cavity 14. This may be accomplished by attaching the sensors to the sheathing 18 or the netting 16, as shown in FIGS. 3A or 3B. When the insulation 20 is blown into the cavity 14, the sensor 32 senses the force F of the insulation. In accordance with this embodiment, a measurement of force F may be taken from within the cavity 14 via a physical or wireless connection, not shown, by the sensor 32.

Figure 4:
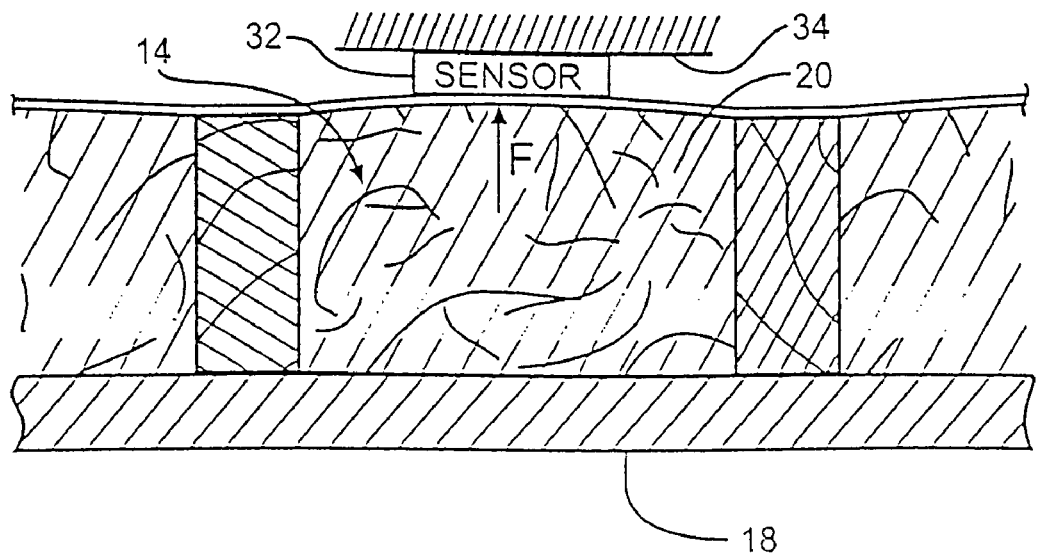
FIG. 4 is a schematic representation in plan of a fixture for supporting a sensor according to the invention outside the cavity.

In another embodiment of the invention, the sensor 32 is supported against the netting 16 and the insulation 20 but is located outside the cavity 14. This can be accomplished in any suitable manner. For example, a fixture 34 could be provided for supporting the sensor 32, as schematically illustrated in FIG. 4 The fixture 34 can be any suitable structure that is adapted to hold the sensor 32 in a substantially fixed position relative to the insulation 20.

Figure 5:
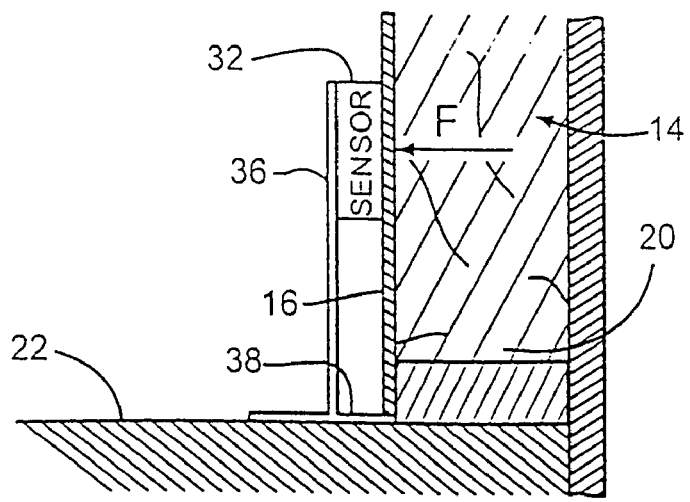
FIG. 5 is a diagrammatic representation in plan of a fixture according to one embodiment of the invention.

In FIG. 5, there is illustrated a fixture in the form of a standard 36 that may be supported by a supporting surface 22 adjacent the cavity 14 with the insulation 20 therein The sensor 32 is adapted to be supported by the standard 36 in a manner so that the sensor 32 can be repeatedly held in a fixed position relative to the netting 16 and the insulation 20. For example, the standard 36 may include a foot 38 for establishing a set distance for the standard 36 away from the netting 16 and the insulation 20.

Figure 6:
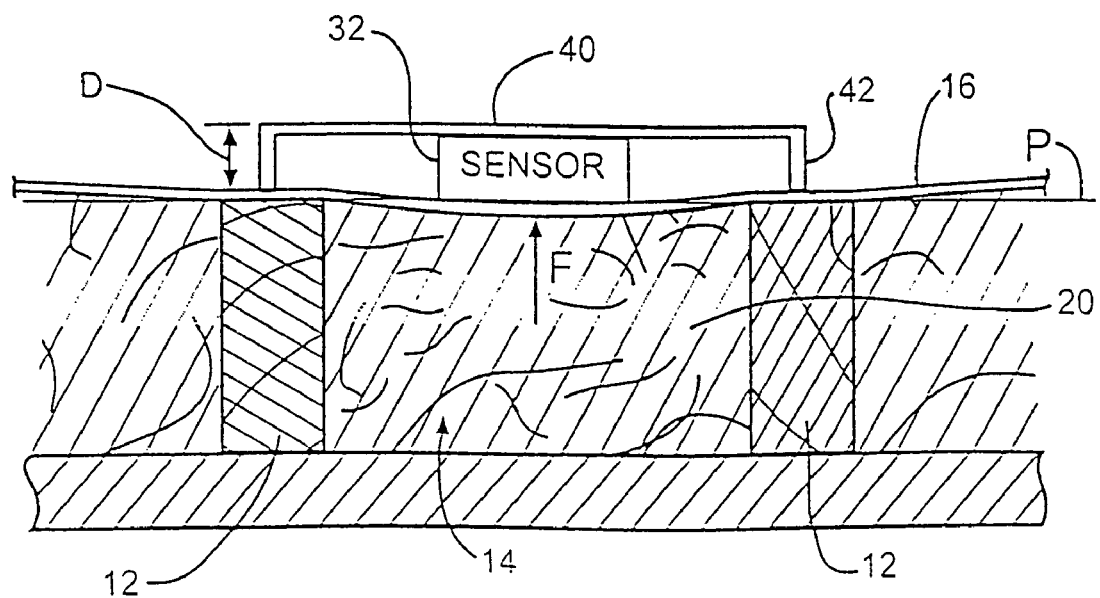
FIG. 6 is a diagrammatic representation in plan of a fixture according to another embodiment of the invention.

In FIG. 6, there is illustrated a fixture in the form of a plate 40 that is adapted to be repeatedly held in a fixed position relative to the netting 16 and the insulation 20. The plate 40 can be held in contact with the netting 16 and the insulation 20, or, as shown in FIG. 6, spaced from the netting 16 and the insulation 20, as long as the position is substantially consistent to permit correlated determinations of density to be made. In the illustrated embodiment, the plate 40 is adapted to be held a fixed distance D from the netting 16 and the insulation 20 in the cavity 14 with each determination of density made by the apparatus. This can be accomplished with legs 42 that extend from the plate 40 to engage the flaming members 12, although such is not required. The distance D is preferably a distance whereby the sensor 32 does not extend beyond a plane P that is coplanar with the inner sides of the flaming members 12, or into the cavity 14 between the flaming members 12.

Figure 7:
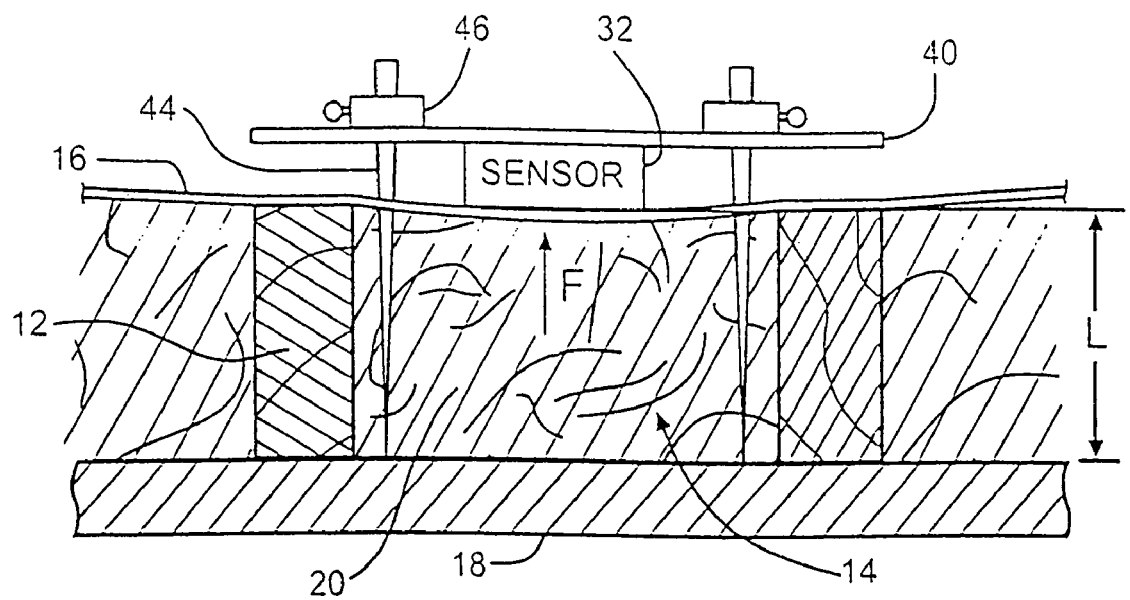
FIG. 7 is a diagrammatic representation in plan of a fixture according to yet another embodiment of the invention.

In FIG. 7, there is illustrated another fixture, which is also in the form of a plate 40. Extending from the plate 40 are pins 44 that are adapted to pierce the netting 16, pass through the insulation 20 in the cavity 14 without substantially affecting its density, and engage the inner side of the sheath 18 The length L of the pins 44 may be fixed or adjustable to accommodate framing members 12 having different dimensions For example, the length L of the pins 44 may be approximately 3-½ inches in length if the flaming members 12 are nominal 2×4 studs or approximately 5-½ inches in length if the framing members 12 are nominal 2×6 ceiling joists. Adjustment of the pins 44 may be accomplished in any suitable manner, such as, for example, providing apertures, not shown, through the plate 40 and a clamp 46 in fixed position relative to the plate 40 and in alignment with the apertures. The pins 44 may pass through the apertures and the clamps 46 may secure the pins 44 in a desired position relative to the plate 40 Alternatively, the pins 44 may be telescopically adjustable, or adjustable in some other suitable manner.

The sensor 32 according to one embodiment of the invention may be in the form of a load cell for measuring the force of the insulation 20 in the cavity 14. Such a sensor 32 would be suitable for use within or outside the cavity 14, as schematically represented in FIGS. 2 and 4, or in any of the embodiments of the invention described herein. Any conventional load cell may be suitable for carrying out the invention.

Figure 8:
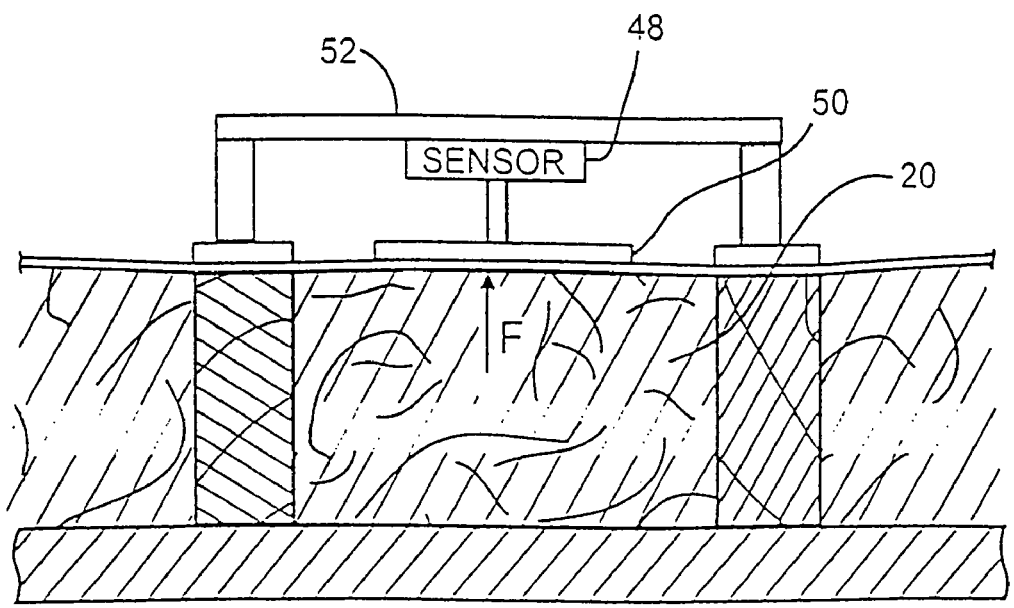
FIG. 8 is a diagrammatic representation in plan of a sensor according to one embodiment of the invention.

In FIG. 8, there is illustrated a sensor in the form of a force transducer 48. The force transducer 48 is adapted to measure the force F encountered by a contact plate 50 held against the insulation 20. The force transducer 48 may be a digital transducer or an analog transducer. The force transducer 48 can be held in a fixed relation to the insulation 20 in any suitable, such as with the use of any of the fixture 52 shown, or any of the fixtures described above. Alternatively, an analog spring-force meter may be used in the place of the force transducer 48. In accordance with the invention, the insulation 20 will exert a force t against the force transducer 48, and that force F will be directly related to the density of the insulation 20.

Figure 9:
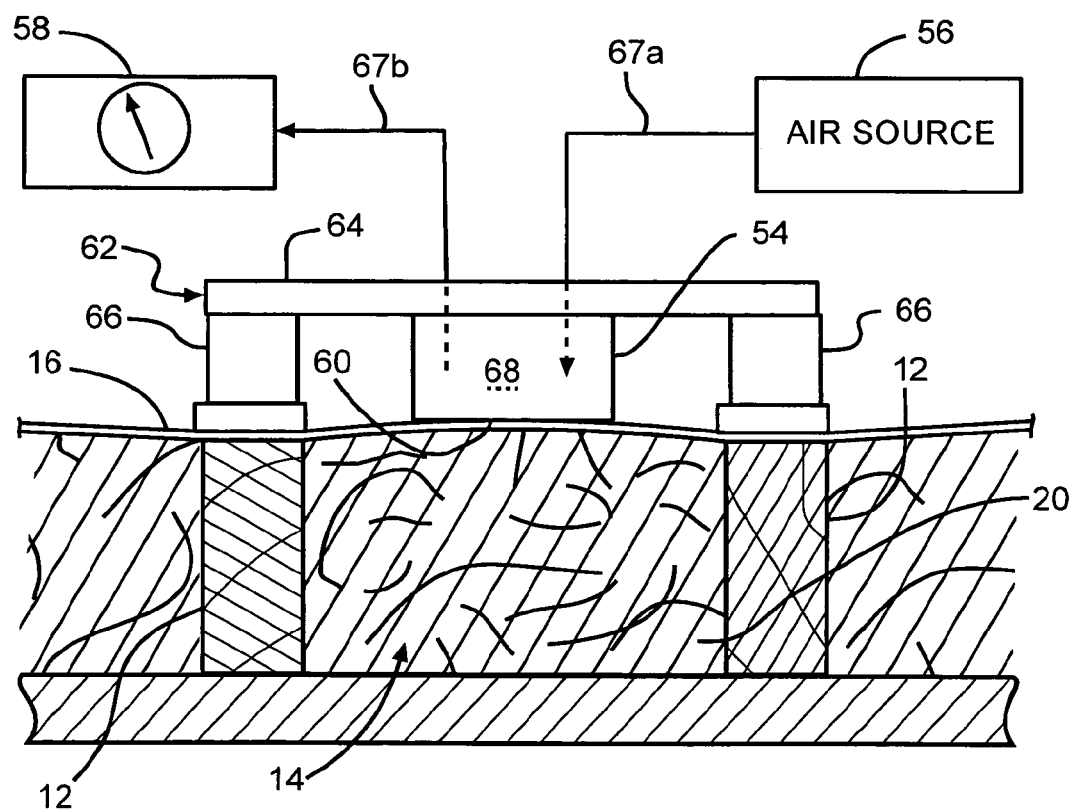
FIG. 9 is a diagrammatic representation in plan of a sensor according to another embodiment of the invention.

In FIG. 9, there is illustrated another embodiment of a sensor in the form of an air cup 54. The air cup 54 includes a contact surface 60. The contact surface 60 is configured to press against the netting 16 and the insulation 20 in the cavity 14 behind the netting 16. As shown in FIG. 9, the air cup 54 can be mounted to an air cup fixture 62. The air cup fixture 62 is configured to support the air cup 54 and hold the air cup 54 in a fixed position relative to the netting 16 and the insulation 20. In the embodiment shown in FIG. 9, the air cup fixture 62 includes an air cup plate 64 and a plurality of air cup legs 66, similar to the plate 40 and legs 42 as shown in FIG. 6. In another embodiment, the air cup fixture 62 could be any suitable structure configured to support the air cup 54 and hold the air cup 54, such as for example, the fixture 36 shown in FIG. 7. In the embodiment shown in FIG. 9, the air cup fixture 62 is mounted to framing members 12, although other mounting methods could be used In yet another embodiment, the air cup fixture 62 could be a free standing structure, such as for example, the fixture 36 shown in FIG. 5. As previously mentioned, the contact surface 60 is configured to press against the netting 16 thereby forming a hollow space 68 within the air cup 54. A pressure differential between the air cup 54 and the atmosphere is created within the air cup 54. The pressure differential may be produced by introducing air, through a source connector 67a, into the air cup 54 from a pressure device 56. The pressure device 56 may be in the form of an air tank, an air pump or any other suitable device to increase the pressure within the air cup 54. Similarly, air may be evacuated from the air cup 54 by air pump, a vacuum, or any other suitable device to decrease the pressure within the air cup 54. As further shown in FIG. 9, a gauge 58 is connected to the air cup 54 by a connector 67b. The gauge 58 is configured to determine the air pressure differential between the air cup 54 and the atmosphere. The gauge 58 is configured to determine the density of the insulation from the air pressure differential by, for example, using a predetermined equation providing the relationship between the air pressure differential and the density of the insulation 20. The pressure in the air cup 54 will be directly related to the density of the insulation 20 behind the netting 16.

Figure 10:
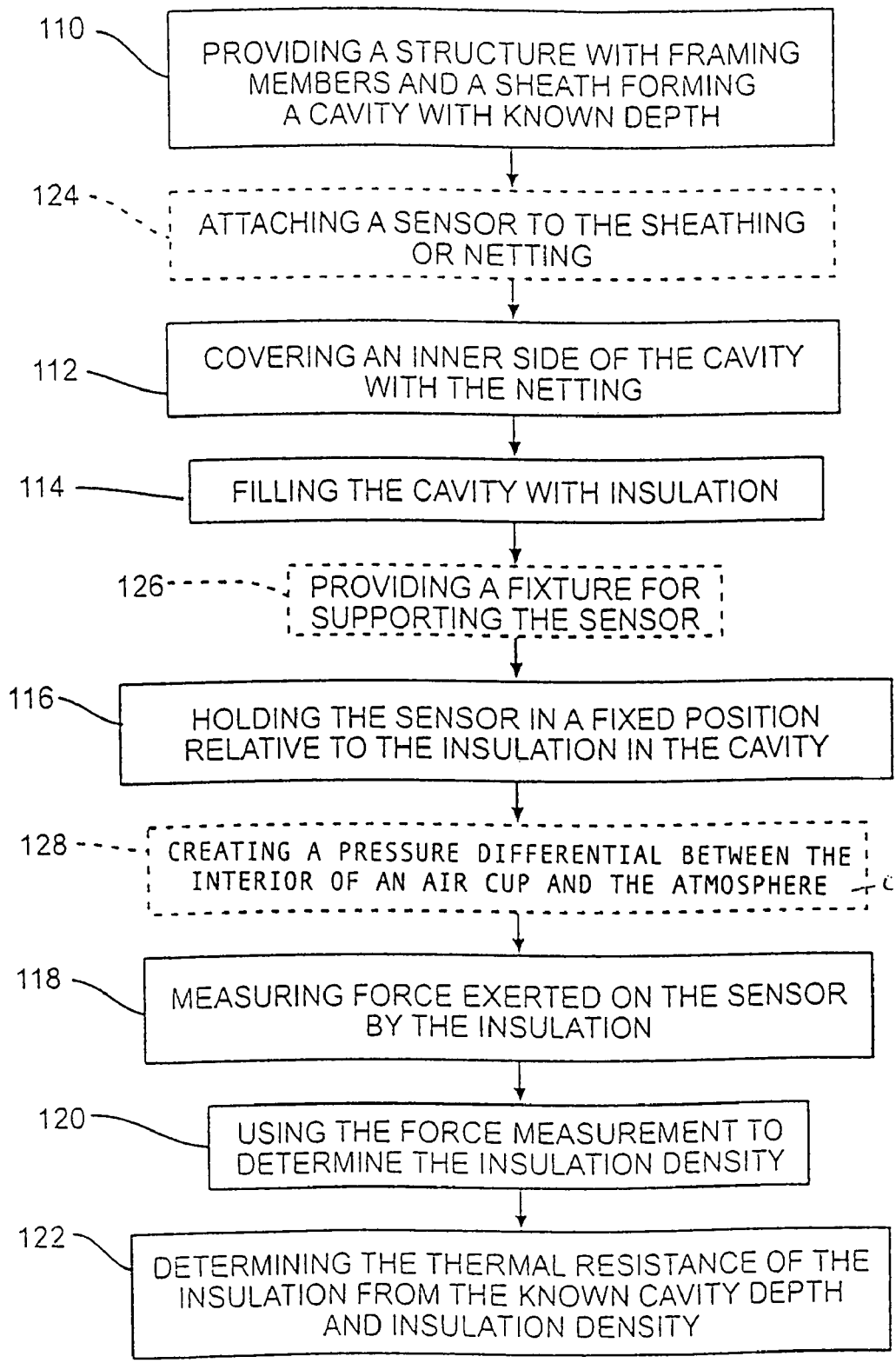
FIG. 10 is a block diagram of a method for determining the density of a loose-fill, blown-in-place fibrous insulation.

In FIG. 10 there is illustrated a method for determining the density of loose-fill, blown-in-place insulation in a cavity defined between framing members of a dwelling or other structure. A method according to a preferred embodiment of the invention may comprise an initial step 110 of providing a structure having framing members and a sheath forming at least one cavity having a known depth of thickness. In step 112, an inner side of the cavity is covered with netting. In step 114, the cavity is filled with insulation. The insulation is preferably a loose-fill, blown-in-place fibrous insulation. The netting is preferably capable of containing the insulation in the cavity while permitting air to escape from the cavity while the cavity is filled with insulation.

In a subsequent step 116, a sensor is held in a substantially fixed position relative to the insulation in the cavity. In step 118, the sensor measures force exerted on the sensor by the insulation. In step 120, the force is used to determine the density of the insulation. In step 122, the thermal resistance of the insulation is determined from the known cavity depth and insulation density.

In optional step 124, the sensor is supported within the cavity. The sensor may be attached to the netting or the sheathing prior to filling the cavity with the insulation. When the insulation is blown into the cavity, the sensor senses the force exerted against the sensor by the insulation.

In an alternative step 126, a fixture is provided for supporting the sensor outside the cavity and holding the sensor in a substantially fixed position relative to the netting and the insulation. The fixture may be in the form of a standard supported by a supporting surface adjacent the cavity and the insulation therein. Alternatively, the fixture may be in the form of a plate that holds the sensor against the netting and insulation. The plate could be held a distance from the flaming members by legs that engage the framing members. Alternatively, the plate could be held a distance from the sheathing by pins that pass through the netting and the insulation and engage the sheathing. The pins could be adjusted in length to accommodate flaming members having different dimensions.

The sensor of step 116 may be in the form of a load cell that senses the force of the insulation against the sensor. Alternatively, the sensor may be a digital or analog force transducer. The transducer can be held in a fixed position relative to the insulation with the fixture provided in step 126. A spring-force meter may be used in the place of the transducer Alternatively, the sensor may be in the form of an air cup that is pressed against the netting and insulation. It will be appreciated that if the sensor provided in step 116 is an air cup, then an optional step 128 may be performed in which a pressure differential between the interior of the air cup and the atmosphere is created. In step 118, the force (air pressure) exerted is then determined by measuring the air pressure in the air cup, such as by using a gauge. The pressure in the air cup is directly related to the density of the insulation behind the netting.

Figure 11:
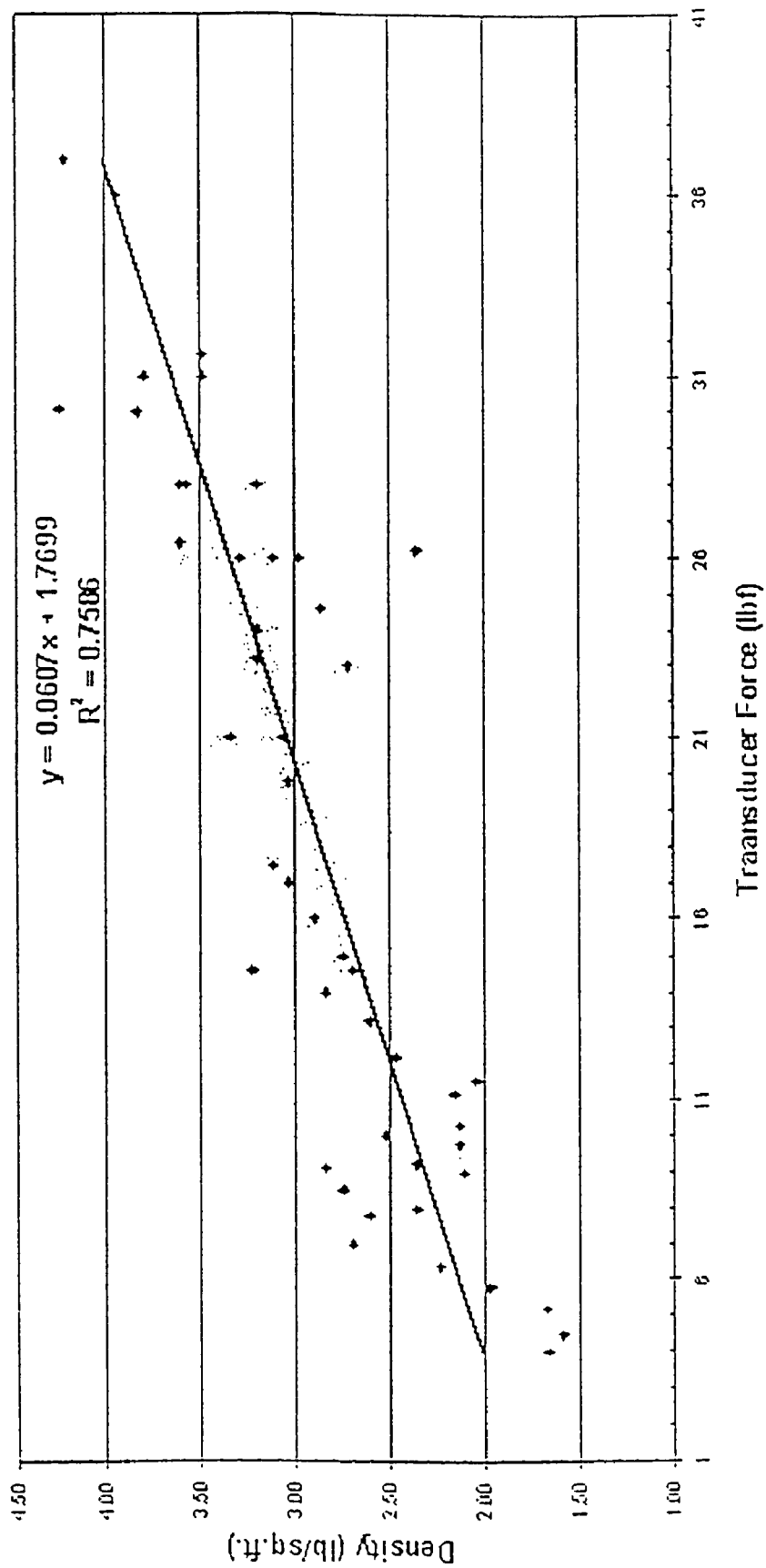
FIG. 11 is graph of empirical data relating to the relationship between the density and the spring force of the loose-fill insulation and a polynomial used in a regression to arrive at the empirical data.

The aforementioned force transducer 48 and spring-force meter rely on the natural spring force of the loose-fill insulation to gage density. As the density of loose-fill insulation increases, the spring force increases proportionally. Using polynomial regression, an empirical relationship can be found between the density and the spring force of the loose-fill insulation. An example of a polynomial and empirical data relating to the relationship between the density and the spring force for is shown in FIG. 11.

Figure 12:
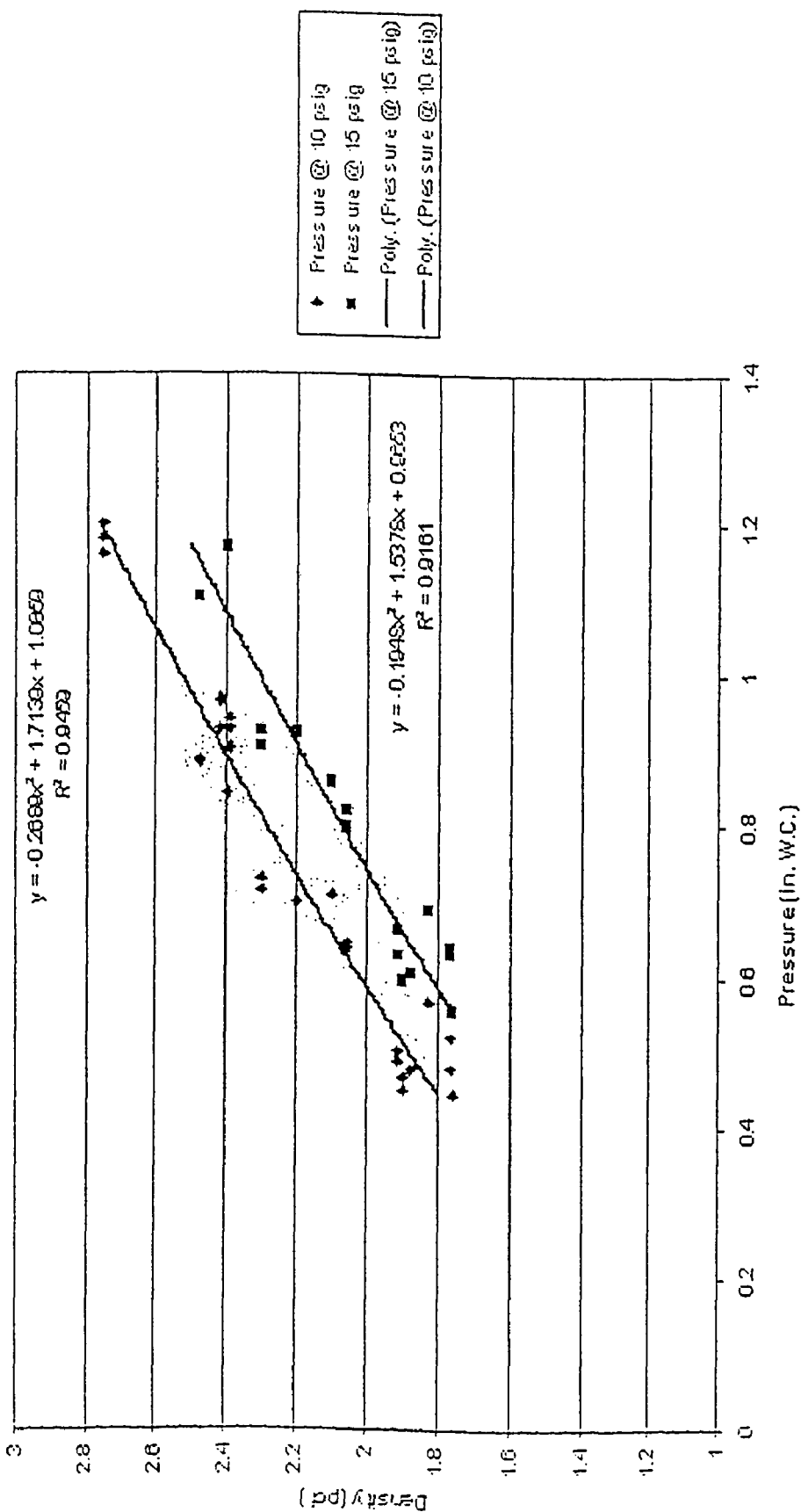
FIG. 12 is graph of empirical data relating to the relationship between the density and the pressure drop through the loose-fill insulation and a polynomial used in a regression to arrive at the empirical data.

The embodiment of the apparatus or method that uses the air cup relies on the natural resistance to flow of the loose-fill insulation to create a pressure drop. For a given source pressure, the loose-fill insulation has a characteristic pressure drop for a given density. Further, back pressure created on the high-pressure side of the loose-fill insulation is directly proportional to density. Using polynomial regression, an empirical relationship can be found between the density and pressure drop. An example of a polynomial and empirical data relating to the relationship between the density and the pressure drop through the insulation is shown in FIG. 12

Factors that can affect either embodiment of the invention include the morphology, diameter, characteristic length, and shape of the fibers of the insulation factors, the binder content, if a binder is used, and other factors that are not mentioned.

The loose-fill thermal conductance, which is inversely proportionate to thermal resistance, can be related to the density by laboratory testing. The data can then curve fitted, as shown in FIGS. 11, and 12.

The invention of this application has been described above both generically and with regard to specific embodiments. Although the invention has been set forth in what is believed to be the preferred embodiments, a wide variety of alternatives known to those of skill in the art can be selected within the generic disclosure. The invention is not otherwise limited, except for the recitation of the claims set forth below.

We claim:

1. An apparatus for determining the density of insulation in an insulation cavity, the insulation cavity being covered by an insulation netting, the apparatus comprising:
    a sensor including (i) an air cup structure having a surface, the surface configured to be pressed against the insulation netting to form a hollow space within the air cup; (ii) an air pressure mechanism connected to the hollow space within the air cup, the air pressure mechanism configured to create an air pressure differential between the hollow space within the air cup and the atmosphere; and (iii) a measuring device connected to the hollow space within the air cup, the measuring device configured to determine the air pressure within the hollow space of the air cup;
    wherein the measuring device is further configured to determine the density of the insulation from the air pressure differential between the hollow space within the air cup and the atmosphere.

2. The apparatus of claim 1 in which the air pressure mechanism is configured to produce the air pressure differential between the hollow space within the air cup and the atmosphere by evacuating air from the air cup.

3. The apparatus of claim 1 in which the measuring device determines the density of the insulation using a predetermined equation providing the relationship between the air pressure differential and the density.

4. The apparatus of claim 1 in which the air pressure mechanism is an air pump.

5. The apparatus of claim 1 wherein the measuring device includes a gauge.

6. The apparatus of claim 1 in which the air cup is mounted to a fixture.

7. The apparatus of claim 6 in which the fixture is configured to be mounted to framing members.

* * * * *